(12) United States Patent
Knight et al.

(10) Patent No.: US 7,886,566 B1
(45) Date of Patent: Feb. 15, 2011

(54) SWAGER DIE AND ACTUATOR MECHANISM

(76) Inventors: Justin Knight, 1222 W. 14th St., Tempe, AZ (US) 85281; Ed Goff, 4718 N. 33rd St., Phoenix, AZ (US) 85018

( * ) Notice: Subject to any disclaimer, the term of this patent is extended or adjusted under 35 U.S.C. 154(b) by 585 days.

(21) Appl. No.: 11/923,419

(22) Filed: Oct. 24, 2007

Related U.S. Application Data (60) Provisional application No. 60/854,025, filed on Oct. 24, 2006.

(51) Int. Cl.
*B21J 7/16* (2006.01)
*B21C 3/06* (2006.01)

(52) U.S. Cl. .............................................. 72/76; 72/468

(58) Field of Classification Search ..................... 72/76, 72/402, 467–468; 29/283.5
See application file for complete search history.

(56) References Cited

U.S. PATENT DOCUMENTS 2,747,442 A * 5/1956 Simpson et al. ................ 72/76

| 6,993,953 | B2 | 2/2006 | Stupecky | |
| 7,010,953 | B2 | 3/2006 | Stupecky | |
| 2004/0096538 | A1 * | 5/2004 | Goff et al. | ................... 425/393 |

* cited by examiner

*Primary Examiner*—Dana Ross
*Assistant Examiner*—Mohammad Yusuf
(74) *Attorney, Agent, or Firm*—Parsons & Goltry; Robert A. Parsons; Michael W. Goltry (57) ABSTRACT

A swager machine and die includes a base with a product holder assembly mounted thereon for linear reciprocating movement between a start and a finished position along an axis of movement. A disc is rotatably mounted on the base and has a swaging die mounted thereon. The swaging die defines a die cavity having an open and a closed position. The die cavity has a longitudinal axis coaxial with an axis of rotation of the disc and coaxial with the axis of movement of the product holder assembly. A hub assembly is rotatably mounted on the disc for relative rotation between the hub assembly and the disc. The hub assembly includes actuating apparatus positioned to engage a portion of the swaging die and move the swaging die from the open to the closed position during relative rotation of the hub assembly and the disc.

22 Claims, 5 Drawing Sheets

SWAGER DIE AND ACTUATOR MECHANISM

FIELD OF THE INVENTION

This invention generally relates to swaging mechanisms and more specifically to mechanisms for swaging cylindrical marker bands onto polymer tubes utilized as components of balloon catheter assemblies.

BACKGROUND OF THE INVENTION

During surgery, using an x-ray machine, a surgeon may locate the position of a balloon catheter in a person's body by detecting the position of radio-opaque marker bands which are swaged onto a balloon catheter.

Swaging is defined as bending or shaping a material by forging or squeezing. Many Swaging machines exist, however many of them are not well suited to swaging marker bands on polymer catheters. Swaging metal bands on polymer catheters is challenging for several reasons. First, the manufacturing of the balloon catheter must take place in a clean environment since it is to be used in the human body. This requires that the swaging machine operate without exuding contaminants onto the catheter components or the surrounding area. Usually, catheters are made in a cleanroom. Cleanrooms are expensive to construct and operate and are therefore, limited in size. Since the swaging machine will be located in a cleanroom, it is best if the machine is small. Last, many swaging machines in addition to being large and dirty are very loud which also limits their use in a cleanroom.

It would be highly advantageous, therefore, to remedy the foregoing and other deficiencies inherent in the prior art.

Accordingly, it is an object of the present invention to provide a new and improved swager machine and die.

Another object of the invention is to provide a new and improved swager machine and die for swaging marker bands on catheters for use in the medical industry.

Another object of the invention is to provide a new and improved swager machine and die for use in clean rooms and similar medical facilities that do not use externally lubricated components.

SUMMARY OF THE INVENTION

Briefly, to achieve the desired objects of the present invention in accordance with a preferred embodiment thereof provided is a Swager machine and die. The swaging die defines a die cavity having an open and a closed position and a longitudinal axis. An elongated gap is defined in the swaging die and separates the swaging die into a first flexure portion and a second flexure portion. The elongated gap extends transversely through the die cavity so as to separate the die cavity into a first cavity portion positioned in the first flexure portion and a second cavity portion positioned in the second flexure portion. The first cavity portion and the second cavity portion are separated by the elongated gap in the open position of the swaging die and substantially abutting in the closed position of the swaging die. Actuating apparatus is positioned to engage a portion of the swaging die and move the swaging die from the open to the closed position.

In a specific aspect, the swager machine includes a base with a product holder assembly mounted thereon for linear reciprocating movement between a start and a finished position along an axis of movement. A disc is rotatably mounted on the base and has a swaging die mounted thereon. The swaging die defines a die cavity having an open and a closed position. The die cavity has a longitudinal axis coaxial with an axis of rotation of the disc and coaxial with the axis of movement of the product holder assembly. A hub assembly is rotatably mounted on the disc for relative rotation between the hub assembly and the disc. The hub assembly includes actuating apparatus positioned to engage a portion of the swaging die and move the swaging die from the open to the closed position during relative rotation of the hub assembly and the disc.

The desired objects of the present invention are further achieved in a preferred embodiment of a swager machine and die including a base and a motor mounted on the base. A product holder assembly is mounted on the base for linear reciprocating movement between a start and a finished position along an axis of movement. A disc is mounted on the base and rotatably coupled to the motor about a rotational axis. A swaging die is mounted on the disc by a plurality of mating aligning dowels and dowel receiving holes positioned in the swaging die and the disc. The swaging die defines a die cavity having an open and a closed position and a longitudinal axis. The swaging die is positioned on the disc with the longitudinal axis of the die cavity coaxial with the axis of rotation of the disc and coaxial with the axis of movement of the product holder assembly. An elongated gap defined in the swaging die separates the swaging die into a first flexure portion and a second flexure portion. The elongated gap extends transversely through the die cavity so as to separate the die cavity into a first cavity portion positioned in the first flexure portion and a second cavity portion positioned in the second flexure portion. The first cavity portion and the second cavity portion are separated by the elongated gap in the open position of the swaging die and substantially abutting in the closed position of the swaging die. A hub assembly is rotatably mounted on the disc for relative rotation between the hub assembly and the disc. The hub assembly is rotatably coupled to the motor for rotation in a direction opposite the rotation of the disc. The hub assembly includes actuating apparatus positioned to engage a portion of the swaging die and move the swaging die from the open to the closed position during relative rotation of the hub assembly and the disc.

BRIEF DESCRIPTION OF THE DRAWINGS

The foregoing and further and more specific objects and advantages of the instant invention will become readily apparent to those skilled in the art from the following detailed description of a preferred embodiment thereof taken in conjunction with the drawings, in which.

DETAILED DESCRIPTION OF A PREFERRED EMBODIMENT

Figure 1:
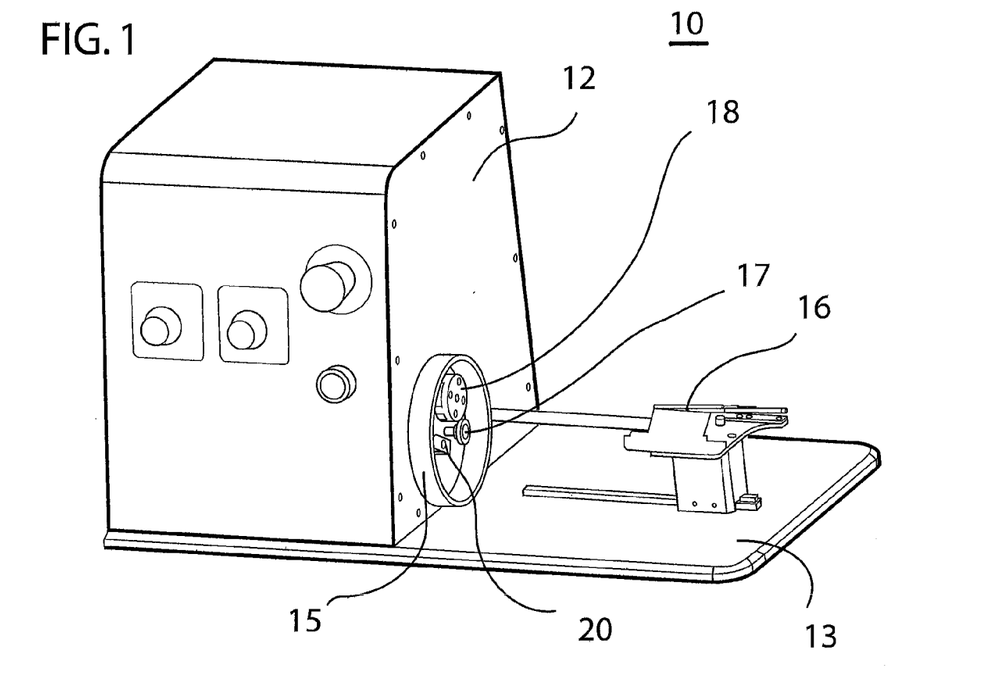
FIG. 1 is a perspective view illustrating a rotary swaging device in accordance with the present invention.

Turning now to the drawings in which like reference characters indicated corresponding elements through out the several views, attention is first directed to FIG. 1 which illustrates a rotary swager device generally designated 10. Rotary swager device 10 includes a housing 12 mounted on a base 13 and containing a die activation assembly 24 (see FIG. 2). A catheter holder assembly 16 is carried by base 13 for reciprocating movement toward a swager assembly 15. Swager assembly 15 includes a hub assembly 18 with die actuating apparatus, a swager die 20 having a die cavity 47 (see FIG. 6) and a funnel 17 aligned with die cavity 47. Catheter holder assembly 16 holds a product-to-be-swaged concentric with funnel 17, which purpose will be described presently.

Figure 2:
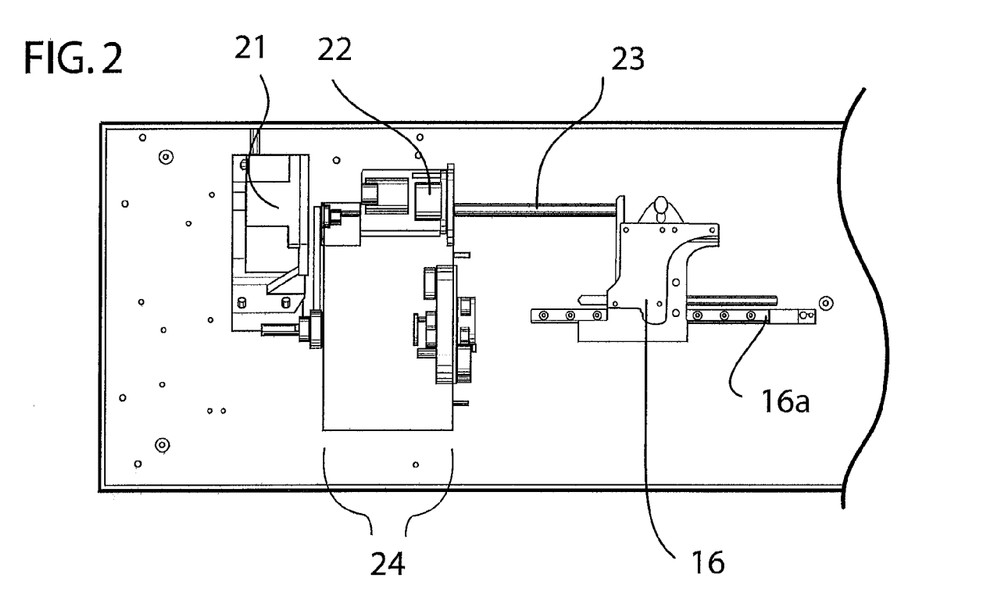
FIG. 2 is a top plan view of the device of FIG. 1 with the housing removed.

With additional reference to FIG. 2, catheter holder assembly 16 is reciprocally moveable along a track 16a carried by base 13 by a linear actuator screw 23 which is activated by a linear actuator motor 22. Thus, as catheter holder assembly 16 is moved toward swager assembly 15 the product-to-be-swaged is fed through funnel 17 and into die cavity 47. While catheter holder assembly 16 feeds the product-to-be-swaged into swager die 20, die activation assembly 24 is activated by engaging a die activation motor 21. Details pertaining to die activation assembly 24 configuration and function is discussed further below.

Figure 3:
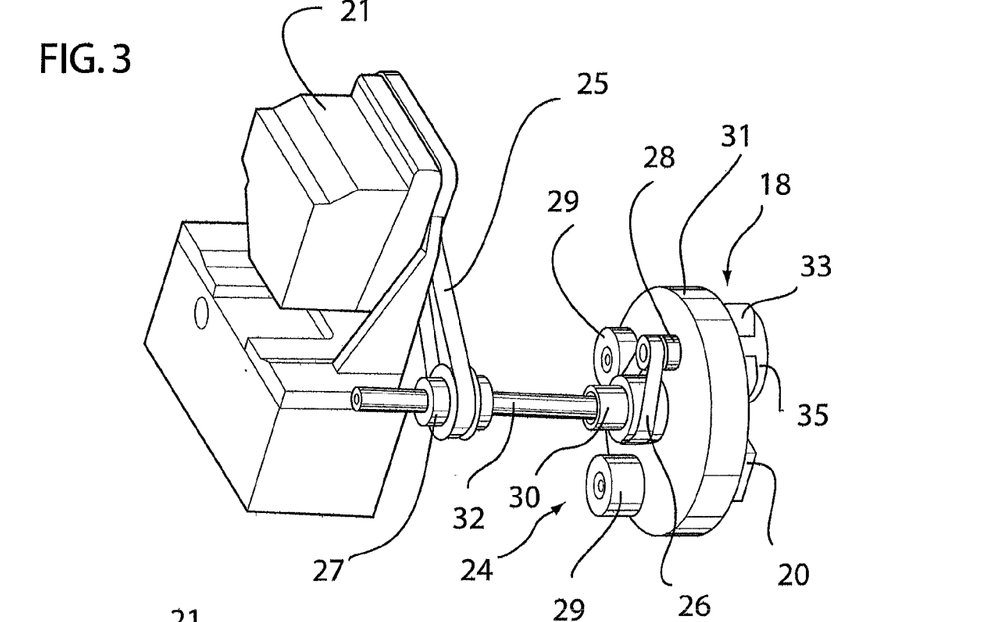
FIG. 3 is a perspective view of the die activation assembly with the bearing block removed for clarity.
Figure 4:
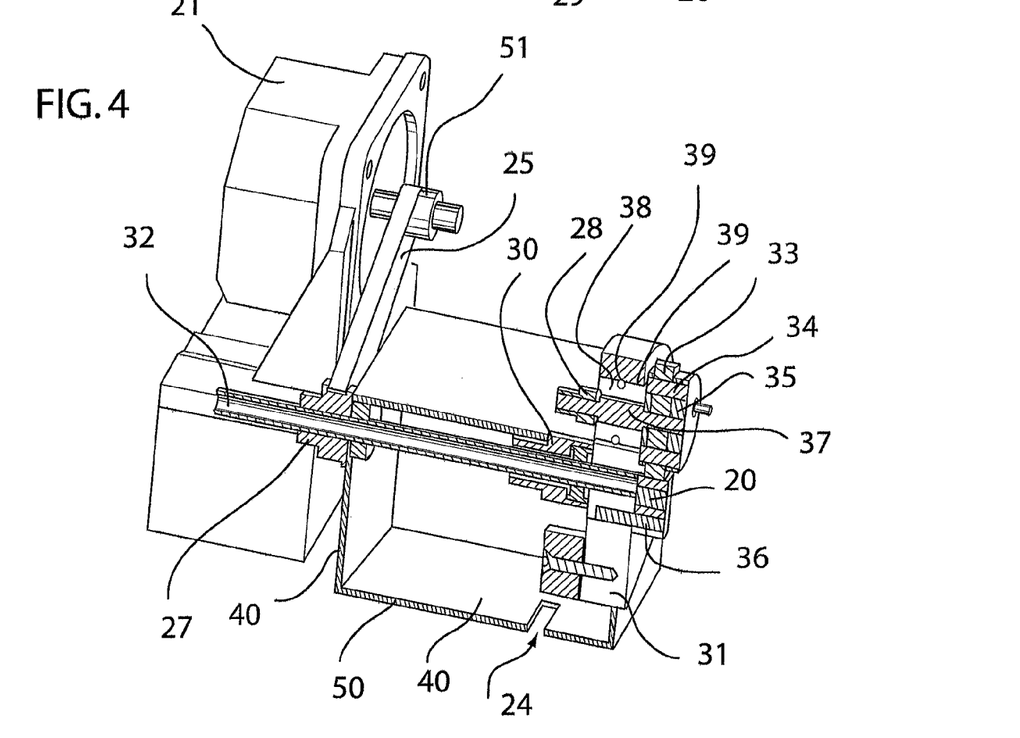
FIG. 4 is a section view of the die activation assembly with the bearing block included.

Referring to FIGS. 2-4, as die activation motor 21 turns, a die activation timing pulley 51 turns a large timing belt 25. Large timing belt 25 rotates a large timing pulley 27 which is rigidly attached to a hollow shaft 32 which rotates as well. Hollow shaft 32 is supported within a bearing block 50 by two hollow shaft bearings 40. Hollow shaft 32 is pressed into a disc 31 so disc 31 rotates in the same direction as the activation motor timing pulley 51. In order to balance the weight of disc 31 and the components mounted to it as they rotate, two counterweights 29 are mounted to the rear face of disc 31. Concentrically mounted around hollow shaft 32 is a central timing pulley 30 that is pressed into bearing block 50, or otherwise fixedly positioned (as, for example, by fixing to the rear surface of disc 31), so as not to rotate with hollow shaft 32.

Figure 5:
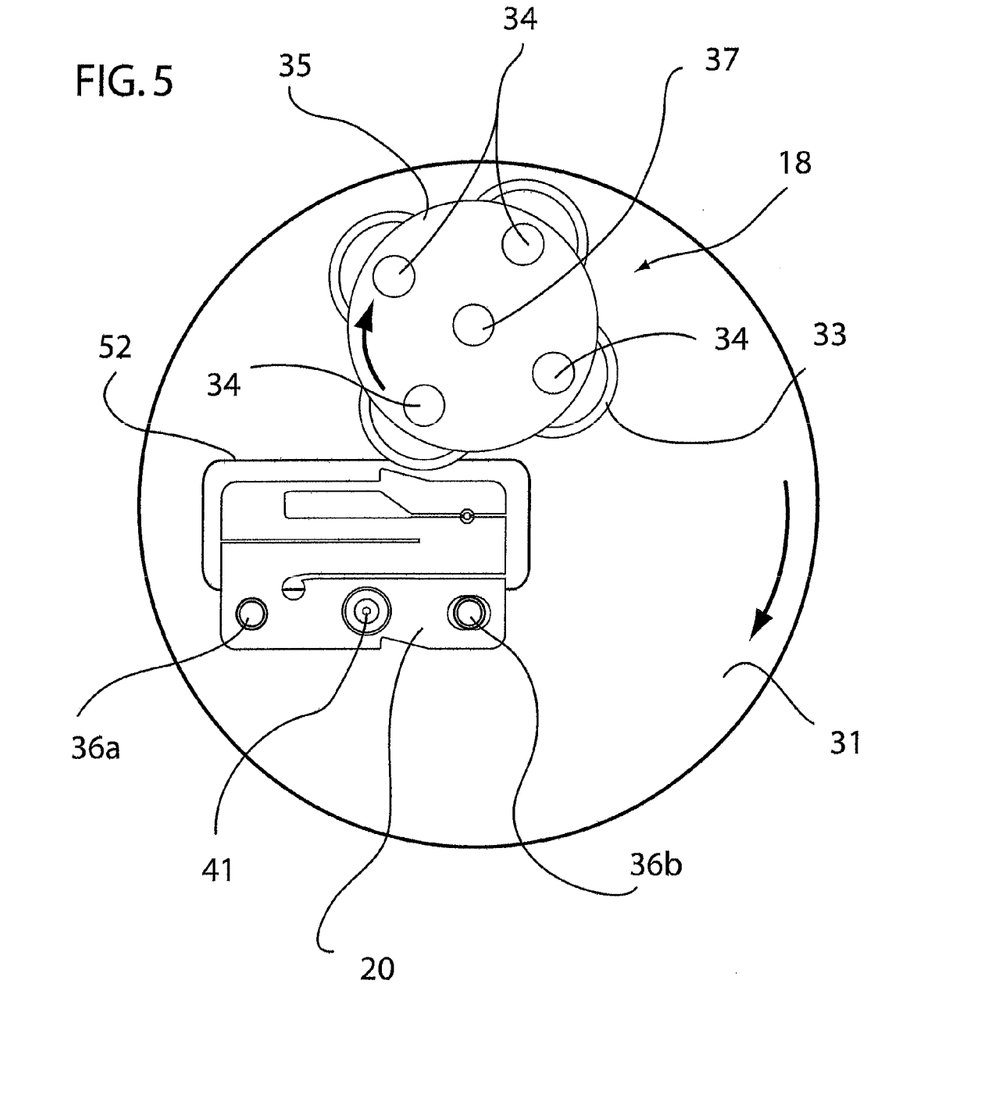
FIG. 5 is a front view of the disc, die, and hub assembly.

Hub assembly 18 with die actuating apparatus positioned thereon is rotatably mounted on disc 31. In this embodiment, the die actuating apparatus on hub assembly 18 includes four die rolling bearing shafts 34 pressed into hub 35 adjacent the outer periphery. Die rolling bearing shafts 34 are configured 90 degrees from each other around the periphery of hub 35 (illustrated best in FIG. 5). Supported on each of die rolling bearing shafts 34 is a free-spinning die rolling bearing 33. As can be seen in FIGS. 3 and 5, rolling bearings 33 are positioned in cavities formed in hub 35 so only a portion of the outer periphery extends radially outwardly beyond the outer periphery of hub 35.

Hub 35 is rotatably mounted on the front face of disc 31 in a plane parallel with disc 31 by a hub shaft 37 that is pressed into hub 35 so that both components rotate together. Hub shaft 37 extends through disc 31 and is rotatably supported relative to disc 31 by two hub shaft bearings 38 mounted in a bore in disc 31 and separated by a retaining ring 39 therebetween. A small timing pulley 28 is rigidly mounted to the rear end of hub shaft 37 adjacent the rear face of disc 31 for rotation with hub shaft 37. A small timing belt 26 is wrapped around central timing pulley 30 and small timing pulley 28. As disc 31 rotates clockwise with the clockwise rotation of hollow shaft 32, small timing pulley 28 is rotated counter-clockwise by stationary central timing pulley 30, which in turn, rotates hub 35 counter-clockwise as well. While actuating apparatus for actuating swager die 20 is included on hub assembly 18, in this embodiment, it will be understood that other embodiments for actuating, camming, or closing swager die 20 could be devised.

Figure 6:
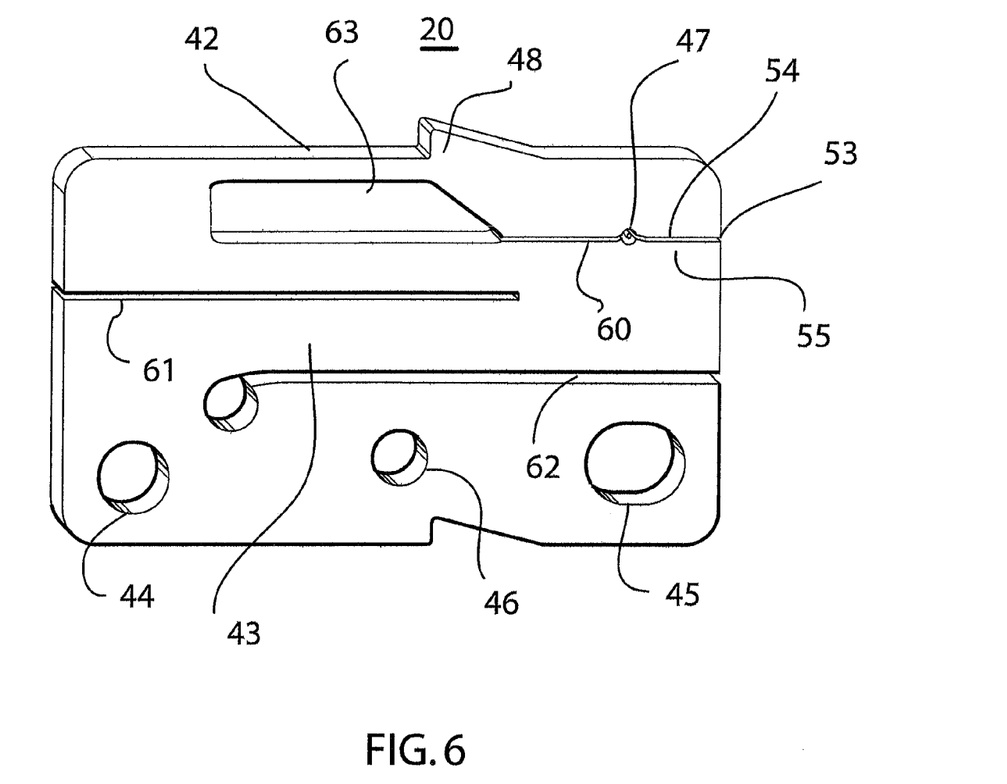
FIG. 6 is an enlarged perspective view of the swager die.

With additional reference to FIG. 6, an enlarged perspective view of swager die 20 is illustrated. In this embodiment, swager die 20 is substantially rectangularly shaped with an alignment hole 44 in a left hand lower corner and an alignment slot 45 in the right hand lower corner. It will be understood that all directions (e.g. upper and lower) used herein for purposes of this explanation are used with reference to FIG. 6 only and could be rotated in actual practice. A mounting hole 46 is positioned at a midpoint between hole 44 and slot 45. A first longitudinally extending slot 60 (also referred to as a die cavity gap) through swager die 20 extends from the right hand edge of swager die 20 approximately 80% of the way to the left hand edge. A second longitudinally extending slot 61 through swager die 20, spaced below slot 60 and parallel thereto, extends from the left hand edge of swager die 20 approximately 80% of the way to the right hand edge. A third longitudinally extending slot 62, spaced below slot 61 and parallel thereto, through swager die 20 extends from the right hand edge of swager die 20 approximately 80% of the way to the left hand edge. First slot 60 is expanded for a substantial portion, designated 63, for relief and to allow additional flexing, as will be explained presently. Also, first slot 60 extends through die cavity 47, essentially splitting die cavity 47 into two separate and spaced apart semicircles, with the longitudinal axis of die cavity 47 lying in first slot 60 and extending transversely therethrough. A ramped die surface 48 is formed in the upper surface of swager die 20, which ramps upwardly as it extends from the right hand edge toward the center. In this embodiment ramped surface 48 is considered a portion of the die actuating apparatus, along with rollers 33 and components moving rollers 33.

The three slots 60, 61, and 62 divide swager die 20 into a top flexure 42 and a bottom flexure 43. First longitudinally extending slot 60 defines a die cavity gap 53 extending from the left hand edge of swager die 20 to die cavity 47. The upper surface of die cavity gap 53 forms an upper flexure landing 54 and the lower surface of die cavity gap 53 forms a lower flexure landing 55. Flexures 42 and 43 flex or move under pressure (activation) on ramped die surface 48 in a limited downward direction, the movement being limited by the transverse width of slots 60, 61, and 62. Swager die 20 is formed of a springy, resilient material, such as stainless steel, hard plastic, etc., which allows flexing of flexures 42 and 43 under force (activation) and returns to the normal position when the force is removed.

Figure 7:
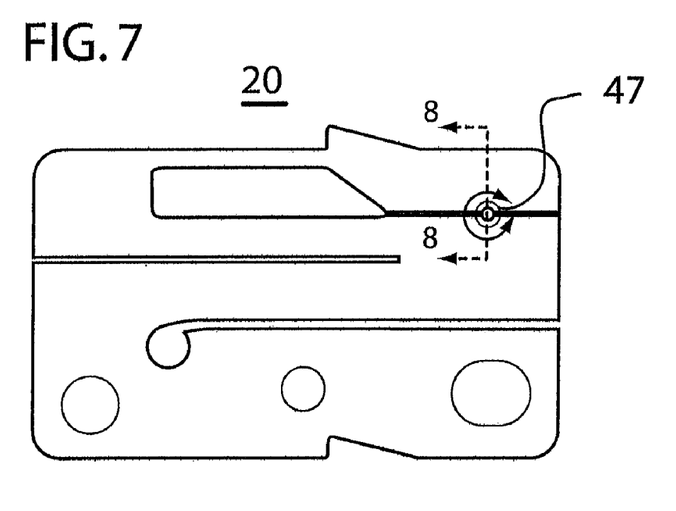
FIG. 7 is a plan view of the swager die.
Figure 8:
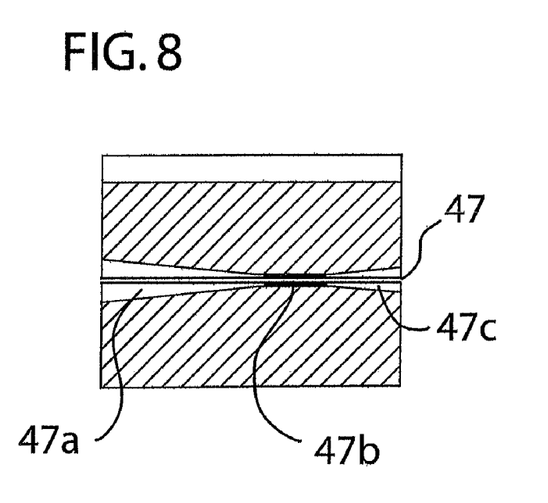
FIG. 8 is a sectional view taken along lines A-A of FIG. 7.

Referring additionally to FIGS. 7 and 8, the structure of die cavity 47 is illustrated in more detail. Die cavity 47 has an axially extending lead-in taper 47a (seen best in FIG. 8), which enables the diameter of the product to be reduced gradually during swaging. Here it will be understood that lead-in taper 47a is either funnel 17 (illustrated in FIG. 1) or is an axial extension of funnel 17. Continuing axially from lead-in taper 47 is a straight cylindrical section 47b, which has approximately the same diameter as the desired finished diameter of the product-to-be-swaged. After straight cylindrical section 47b, is another axially extending taper 47c which allows the swaged product to freely enter (return outwardly) through swager die 20 from the rear.

Referring again to FIG. 5, two die aligning dowels 36a and 36b are pressed into the front face of disc 31 and are very accurately located relative to hub 35 as well as the rotary axis of disc 31. Swager die 20 is attached to disc 31 by aligning dowel pin hole 44 with die dowel 36a, and by aligning dowel pin slot 45 with die dowel 36b. Swager die 20 is then secured by inserting a die holding screw 41 into screw mount hole 46 and threadedly engaging it in a tapped hole in the front face of disc 31. Behind swager die 20 is a disc relief 52 which fits in a shallow depression in disc 31 that allows top flexure 42 and bottom flexure 43 to move freely as die 20 is activated.

It will be understood that die 20 can be employed to swag many different items, such as plastic tubes, metals tubes, solid cylindrical objects and the like. As a specific example, the tip of a solid plastic catheter can be swagged using the present device for various reasons. In the operation of rotary swager device 10 of the present embodiment, a product-to-be-swaged is fixed in catheter holder assembly 16 for longitudinal movement along the axis of die cavity 47. Linear actuator motor 22 is activated to rotate linear actuator screw 23 and gradually move the product-to-be-swaged into funnel 17, i.e. die cavity 47. Simultaneously, die activation motor 21 is activated and rotates disc 31, which, in turn, rotates die 20 relative to the product-to-be-swaged. Hub 35 also rotates, in a direction that is the reverse of the rotation of disc 31, in a timed manner with respect to swager die 20. In response to the rotation of hub 35, each of the four die rolling bearings 33 rolls against ramped die surface 48 of swager die 20. As a die rolling bearing 33 comes into contact with ramped die surface 48, top flexure 42 is deflected downward which biases die cavity gap 53 toward a closed position.

As the top semicircle or portion of die cavity 47 is deflected downward it comes into contact with the product-to-be-swaged which is supported on its bottom by the lower semicircle or bottom portion of die cavity 47. The lead-in taper 47a of die cavity 47 enables the diameter of the product-to-be-swaged to be reduced gradually during swaging. After lead-in taper 47a, straight cylindrical section 47b has approximately the desired diameter of the finished or swaged product. Once the top portion of die cavity 47 comes into contact with the product-to-be-swaged, bottom flexure 43 begins to deflect downward but will continue to decrease die cavity gap 53 until upper flexure landing 54 makes contact with lower flexure landing 55.

Figure 9:
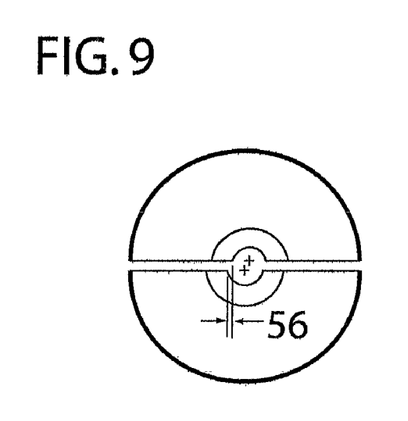
FIG. 9 is a front view of the die cavity.

Once this occurs the upper and lower semicircles or portions of die cavity 47 will align even though top flexure 42 initially moves without bottom flexure 43 moving, producing a slight relative longitudinal movement. This is possible because the upper semicircle or portion of die cavity 47 has a lateral offset, designated 56, from the lower semicircle or portion of the die cavity as shown in FIG. 9. In practice, lateral offset 56 is smaller than the width of die cavity gap 53. After flexure landings 54 and 55 make contact, they will continue to deflect together (through flexure or movement of bottom flexure 43) until die rolling bearing 33 has rolled directly over die cavity 47 on ramped die surface 48.

Since the amount of deflection of the flexures can be accurately controlled by the die activation apparatus and the width, height, and length of the flexures can be controlled by design, the swaging force may be calculated easily from well known beam equations. This is an advantage over existing swage methods because the die activation apparatus can be optimized for the predicted swage force, making the mechanism smaller and more durable. Also, the mass of the die landings and the spring constants of the flexures are designed such that the spring-mass system will not reach resonance at relatively high swaging frequencies, enabling the swaging machine to swage at higher frequencies compared to existing swaging machines (i.e. 100 hertz).

The relative movement or timing between linear actuator motor 22 and die activation motor 21 is such that a plurality of swaging rotations occur per predetermined amount of linear movement of the product-to-be-swaged. In different applications the amount of pressure required for the swaging may differ and, accordingly, controls for linear actuator motor 22 and die activation motor 21 may be included on housing 12 (see FIG. 1) to adjust relative speeds for optimum swaging. The final taper 47c allows the swaged product to be removed from swager die 20 in a reverse direction, after moving completely through swager die 20. Linear actuator motor 22 and die activation motor 21 are described in this embodiment for convenience of operation it will be understood, however, that other motive means might be utilized, such as an inter-geared single motor, hand operation, etc.

Thus, a new and novel swager die and actuator mechanism has been disclosed. This swager die has several advantages over prior art. First, it consists of one component, a wire electric discharge machined piece of hardened stainless steel in the preferred embodiment, which is unlike the two prior art structures discussed earlier. Second, the movement of the die is determined by its geometry instead of the interaction of dowel pins in holes which may lead to binding as detailed in the Stupecky patents, U.S. Pat. No. 6,993,953 and U.S. Pat. No. 7,010,953.

This new swager die actuator mechanism also has advantages over prior art. First, the actuator mechanism does not require any externally lubricated components that may contaminate the product-to-be-swaged or surrounding area as in the prior art of the Torrington Model 100 rotary swager. Second, the die actuator is able to apply higher frequency swages without a drop-off in swage force as in prior art type mechanisms similar to that depicted in the Stupecky patent. This is because the swage force in the new swager mechanism is dependant upon the deflection of the bottom flexure 43, the flexure's geometry, and material modulus of elasticity, all of which do not change with frequency up to the resonant frequency. Therefore, the new swager die actuator is able to close and open the die more often, which decreases the time taken to swage a product. Last, this new swager die actuator mechanism is small, quiet, and clean enough to be used in a clean room as is required for the production of catheter balloons.

Various changes and modifications to the embodiment herein chosen for purposes of illustration will readily occur to those skilled in the art. To the extent that such modifications and variations do not depart from the spirit of the invention, they are intended to be included within the scope thereof, which is assessed only by a fair interpretation of the following claims.

Having fully described the invention in such clear and concise terms as to enable those skilled in the art to understand and practice the same, the invention claimed is:

1. Swager machine and die comprising:
   a swaging die defining a die cavity having an open and a closed position and a longitudinal axis, an elongated gap defined in the swaging die and separating the swaging die into a first flexure portion and a second flexure portion, the elongated gap extending transversely through the die cavity so as to separate the die cavity into a first cavity portion positioned in the first flexure portion and a second cavity portion positioned in the second flexure portion, the first cavity portion and the second cavity portion being separated by the elongated gap in the open position of the swaging die and substantially abutting in the closed position of the swaging die; and
   actuating apparatus positioned to engage a portion of the swaging die and move the swaging die from the open to the closed position.

2. Swager machine and die as claimed in claim 1 further including a base and a disc rotatably mounted on the base, the swaging die mounted on the disc, the longitudinal axis of the die cavity coaxial with an axis of rotation of the disc.

3. Swager machine and die as claimed in claim 2 further including a product holder assembly mounted on the base for linear reciprocating movement between a start and a finished position along an axis of movement coaxial with the axis of rotation of the disc.

4. Swager machine and die as claimed in claim 2 further including a hub assembly rotatably mounted on the disc for relative rotation between the hub assembly and the disc, the hub assembly including the actuating apparatus positioned to engage a portion of the swaging die and move the swaging die from the open to the closed position during relative rotation of the hub assembly and the disc.

5. Swager machine and die as claimed in claim 4 wherein the actuating apparatus includes a plurality of rollers rotatably mounted on a hub and positioned to engage a ramped surface on the swaging die to urge the swaging die into the closed position.

6. Swager machine and die as claimed in claim 4 wherein the disc is driven rotatably in a first direction by a motor and the hub is driven rotatably in an opposite direction by the motor.

7. Swager machine and die as claimed in claim 1 wherein the first cavity portion and the second cavity portion move a short distance laterally between the open position and the closed position, and the first cavity portion and the second cavity portion are transversely offset the short distance in the open position so that the first cavity portion and the second cavity portion are aligned in the closed position.

8. Swager machine and die as claimed in claim 1 wherein the swaging die includes a plurality of elongated gaps defined therein, the plurality of gaps separating the die into an upper flexure portion and a lower flexure portion.

9. Swager machine and die as claimed in claim 8 wherein the plurality of elongated gaps extend into the swaging die alternately from opposite edges to form the upper flexure portion and the lower flexure portion.

10. Swager machine and die as claimed in claim 1 wherein the die cavity defined by the swaging die includes a tapered inlet opening and a straight cylindrical section, with the tapered inlet opening tapering radially inwardly from an enlarged outer opening to the straight cylindrical section.

11. Swager machine and die comprising:
a base;
a product holder assembly mounted on the base for linear reciprocating movement between a start and a finished position along an axis of movement;
a disc rotatably mounted on the base and having a swaging die mounted thereon, the swaging die defining a die cavity having an open and a closed position, the die cavity having a longitudinal axis coaxial with an axis of rotation of the disc and coaxial with the axis of movement of the product holder assembly; and
a hub assembly rotatably mounted on the disc for relative rotation between the hub assembly and the disc, the hub assembly including actuating apparatus positioned to engage a portion of the swaging die and move the swaging die from the open to the closed position during relative rotation of the hub assembly and the disc;
wherein the swaging die includes an elongated gap defined therein separating the die into a first flexure portion and a second flexure portion.

12. Swager machine and die as claimed in claim 11 wherein the actuating apparatus includes a plurality of rollers rotatably mounted on a hub and positioned to engage a ramped surface on the swaging die to urge the swaging die into the closed position.

13. Swager machine and die as claimed in claim 11 wherein the disc is driven rotatably in a first direction by a motor and the hub is driven rotatably in an opposite direction by the motor.

14. Swager machine and die as claimed in claim 11 wherein the elongated gap extends transversely through the die cavity separating the die cavity into a first cavity portion positioned in the first flexure portion and a second cavity portion positioned in the second flexure portion, the first cavity portion and the second cavity portion being separated by the elongated gap in the open position of the swaging die and substantially abutting in the closed position of the swaging die.

15. Swager machine and die as claimed in claim 11 wherein the first cavity portion and the second cavity portion move a short distance laterally between the open position and the closed position, and the first cavity portion and the second cavity portion are transversely offset the short distance in the open position so that the first cavity portion and the second cavity portion are aligned in the closed position.

16. Swager machine and die as claimed in claim 11 wherein the swaging die includes a plurality of elongated gaps defined therein, the plurality of gaps separating the die into an upper flexure portion and a lower flexure portion.

17. Swager machine and die as claimed in claim 16 wherein the plurality of gaps extend into the swaging die alternately from opposite edges to form the upper flexure portion and the lower flexure portion.

18. Swager machine and die as claimed in claim 11 wherein the die cavity defined by the swaging die includes a tapered inlet opening and a straight cylindrical section, with the tapered inlet opening tapering radially inwardly from an enlarged outer opening to the straight cylindrical section.

19. Swager machine and die comprising:
a base;
a motor mounted on the base;
a product holder assembly mounted on the base for linear reciprocating movement between a start and a finished position along an axis of movement;
a disc mounted on the base and rotatably coupled to the motor, the disc having a rotational axis;
a swaging die mounted on the disc, the swaging die defining a die cavity having an open and a closed position and a longitudinal axis, the swaging die positioned on the disc with the longitudinal axis of the die cavity coaxial with the axis of rotation of the disc and coaxial with the axis of movement of the product holder assembly, an elongated gap defined in the swaging die and separating the swaging die into a first flexure portion and a second flexure portion, the elongated gap extending transversely through the die cavity so as to separate the die cavity into a first cavity portion positioned in the first flexure portion and a second cavity portion positioned in the second flexure portion, the first cavity portion and the second cavity portion being separated by the elongated gap in the open position of the swaging die and substantially abutting in the closed position of the swaging die; and
a hub assembly rotatably mounted on the disc for relative rotation between the hub assembly and the disc, the hub assembly being rotatably coupled to the motor for rotation in a direction opposite the rotation of the disc, the hub assembly including actuating apparatus positioned to engage a portion of the swaging die and move the swaging die from the open to the closed position during relative rotation of the hub assembly and the disc.

20. Swager machine and die as claimed in claim 19 wherein the first cavity portion and the second cavity portion move a short distance laterally between the open position and the closed position, and the first cavity portion and the second cavity portion are transversely offset the short distance in the open position so that the first cavity portion and the second cavity portion are aligned in the closed position.

21. Swager machine and die as claimed in claim 19 wherein the actuating apparatus includes a plurality of rollers rotatably mounted on a hub and positioned to engage a ramped surface on the swaging die to urge the swaging die into the closed position.

22. Swager machine and die as claimed in claim 19 wherein the die cavity defined by the swaging die includes a tapered inlet opening and a straight cylindrical section, with the tapered inlet opening tapering radially inwardly from an enlarged outer opening to the straight cylindrical section.

* * * * *